(12) United States Patent
Cannon et al.

(10) Patent No.: US 7,811,325 B2
(45) Date of Patent: Oct. 12, 2010

(54) INTERVERTEBRAL IMPLANT COMPONENT WITH THREE POINTS OF CONTACT

(75) Inventors: Heather Cannon, West Chester, PA (US); Edwin Cham, Schwenksville, PA (US); Thierry Marnay, Casielnau le Lez (FR)

(73) Assignee: Synthes USA, LLC, West Chester, PA (US)

(*) Notice: Subject to any disclaimer, the term of this patent is extended or adjusted under 35 U.S.C. 154(b) by 31 days.

(21) Appl. No.: 12/190,237

(22) Filed: Aug. 12, 2008

(65) Prior Publication Data

US 2008/0300688 A1 Dec. 4, 2008

Related U.S. Application Data

(62) Division of application No. 11/686,021, filed on Mar. 14, 2007, now abandoned.

(51) Int. Cl.
*A61F 2/44* (2006.01)
(52) U.S. Cl. .................. 623/17.14; 623/17.15; 606/279
(58) Field of Classification Search ... 623/17.11–17.16; 606/279
See application file for complete search history.

(56) References Cited

U.S. PATENT DOCUMENTS

| | | | |
|---|---|---|---|
| 5,755,798 | A | 5/1998 | Papavero et al. |
| 2004/0117022 | A1 | 6/2004 | Marnay et al. |
| 2005/0246022 | A1 | 11/2005 | Zubok et al. |
| 2005/0267581 | A1 | 12/2005 | Marnay et al. |
| 2006/0036326 | A1 | 2/2006 | Baumgartner et al. |

*Primary Examiner*—Thomas C Barrett
*Assistant Examiner*—Andrew Yang
(74) *Attorney, Agent, or Firm*—Woodcock Washburn LLP

(57) ABSTRACT

A method of implanting an intervertebral implant or component thereof, in which each component is selected to have an inner surface and an outer surface which engages an adjacent vertebra and presents only three distinct points of contact with a cortical rim of the vertebra. The outer surface is selected to have a footprint which is sized to be within that of the cortical rim. In disclosed embodiments, the footprint can be convexo-concave shaped or kidney shaped. The intervertebral implant can be provided with upper and lower (or first and second) components which engage adjacent first and second vertebrae and which move relative to one another. The implant has both the first and second outer surfaces sized to present a respective footprint sufficient for two lateral-anterior and one posterior points of contact with an adjacent cortical rim of the respective first and second vertebra.

14 Claims, 4 Drawing Sheets

INTERVERTEBRAL IMPLANT COMPONENT WITH THREE POINTS OF CONTACT

CROSS REFERENCE TO RELATED APPLICATIONS

This application is a divisional of application Ser. No. 11/686,021, filed Mar. 14, 2007 now abandoned (which is hereby incorporated by reference).

BACKGROUND OF THE INVENTION

Historically, when it was necessary to completely remove a disc from between adjacent vertebrae, the conventional procedure is to fuse the adjacent vertebrae together. This "spinal fusion" procedure, which is still in use today, is a widely accepted surgical treatment for symptomatic lumbar degenerative disc disease. However, reported clinical results vary considerably, and complication rates are considered by some to be unacceptably high.

More recently, there have been important developments in the field of disc replacement, namely disc arthoplasty, which involves the insertion of an artificial intervertebral disc implant into the intervertebral space between adjacent vertebrae, and which allows limited universal movement of the adjacent vertebrae with respect to each other. The aim of total disc replacement is to remove pain generation (caused by a bad disc), restore anatomy (disc height), and maintain mobility in the functional spinal unit so that the spine remains in an adapted sagittal balance. Sagittal balance is defined as the equilibrium of the trunk with the legs and pelvis to maintain harmonious sagittal curves. In contrast with fusion techniques, total disc replacement preserves mobility in the motion segment and mimics physiologic conditions.

One such intervertebral implant includes an upper part that can communicate with an adjacent vertebrae, a lower part that can communicate with an adjacent vertebrae, and an insert located between these two parts. An example of this type of implant is disclosed in U.S. Pat. No. 5,314,477 (Marnay).

While this and other known implants represent improvements in the art of artificial intervertebral implants, there exists a continuing need for improvements in this field.

BRIEF SUMMARY OF THE INVENTION

In accordance with the present invention, a component of an intervertebral implant is provided with an inner surface and an outer surface. The outer surface engages an adjacent vertebra and presents only three distinct points of contact with a cortical rim of the adjacent vertebra. Preferably, the outer surface has a footprint which is sized to be within that of the cortical rim. In disclosed embodiments, the footprint of the outer surface has a major convex side and can be convexo-concave shaped, D shaped, or kidney shaped.

Preferably, the three points of contact of the footprint of the outer surface with the cortical rim are two lateral-anterior points and one posterior point. In addition, the footprint of the outer surface includes opposed ends which provide the two lateral-anterior points of contact.

In a preferred embodiment, the outer surface of the component includes at least one vertebra engaging protrusion. The protrusion can include a protruding keel located adjacent an opposed or longitudinal end, which keel may be curved.

Also in a preferred embodiment, the inner surface includes a pair of cutouts extending to an adjacent outer edge thereof. The cutouts are preferably angled centrally inwardly and dovetail shaped in cross section.

Also in accordance with the present invention, an intervertebral implant can be provided with upper and lower (or first and second) components, each as described above and each of which engages an adjacent first and second vertebrae. The implant also includes a means for allowing the first and second components to move relative to one another. The implant would have the outer surfaces of both the first and second components sized to present a respective footprint sufficient for only three points of contact with an adjacent cortical rim of the respective first and second vertebra.

It is an advantage of the present invention that a minimally sized intervertebral implant is provided.

It is also an advantage of the present invention that the intervertebral implant has only three points of contact made at the cortical rim of the adjacent vertebrae.

It is a further advantage of the present invention that a major convex-sided shape of the intervertebral implant presents a small insertion size which can be inserted along an arc shaped path.

Other features and advantages of the present invention are stated in or apparent from detailed descriptions of presently preferred embodiments of the invention found hereinbelow.

DETAILED DESCRIPTION OF THE INVENTION

Figure 1:
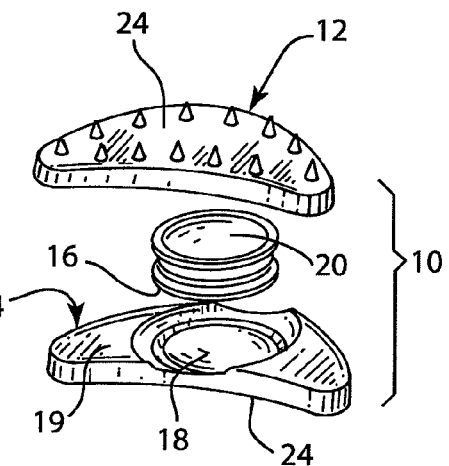
FIG. 1 is a perspective exploded view of an implant in accordance with the present invention.

With reference now to the drawings in which like numerals represent like elements throughout the views, an intervertebral implant 10 according to the present invention is depicted in FIGS. 1-6. Broadly and as best shown in FIG. 1, implant 10 is formed of three components or parts, an upper part 12, a lower part 14 and a movable insert 16 allowing upper part 12 to move relative to lower part 14. An opposed pair of convexities 18 are provided on respective inner surfaces 19 of upper and lower parts 12 and 14 (though only convexity 18 for lower part 16 is shown), and concavities 20 (only upper concavity 20 is shown) on opposite sides of insert 16 which concavities 20 mate with adjacent convexities 18. Such parts 12, 14 and 16 in general and the motions provided thereof are well known in the art, such as in USPA 2006/0116769 (Marnay et al.) which is herein incorporated by reference, and thus need not be discussed further. It will be noted that it is also known in the art that insert 16 could be a convexity extending integrally from one part which mates with a concavity integrally in the other part, so the separate depiction of an insert 16 for the present invention is only exemplary of one type of movable insert means known in the art.

Figure 2:
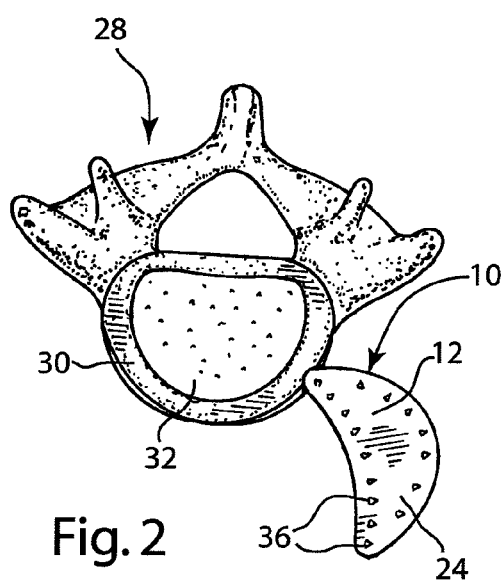
FIG. 2 is a top plan view of the implant depicted in FIG. 1 adjacent a vertebra.
Figure 3:
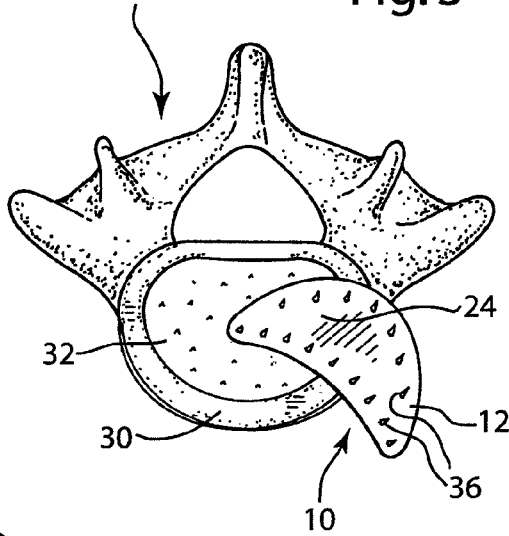
FIG. 3 is a top plan view of the implant depicted in FIG. 2 partially inserted into an intervertebral space.
Figure 4:
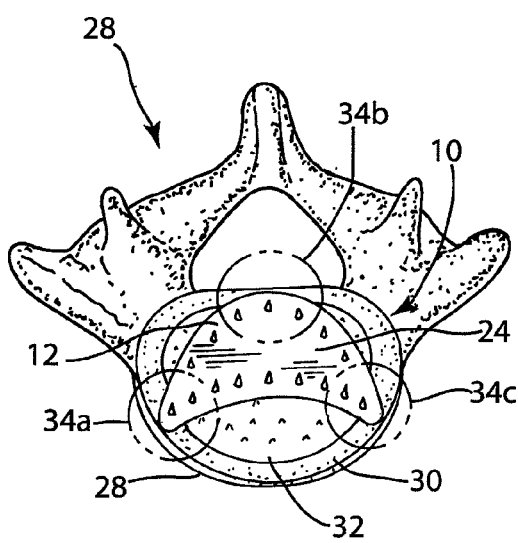
FIG. 4 is a top plan view of the implant depicted in FIG. 2 fully inserted into an intervertebral space.
Figure 5:
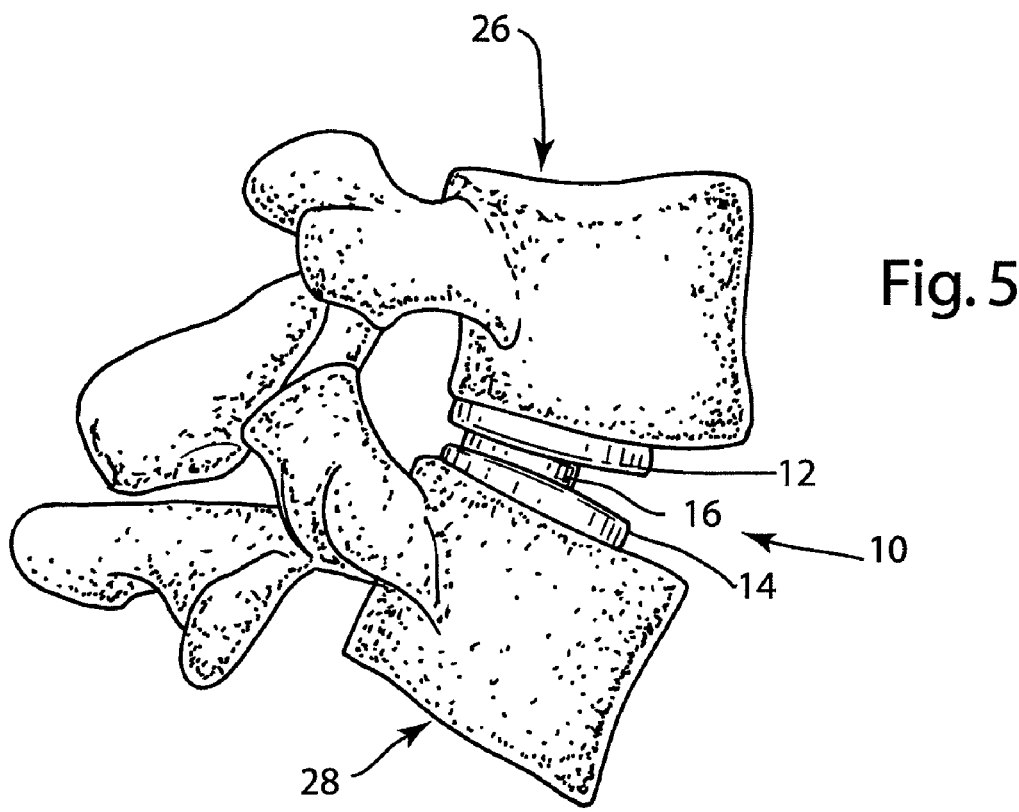
FIG. 5 is a left side view of the implant depicted in FIG. 2 inserted into an intervertebral space.
Figure 6:
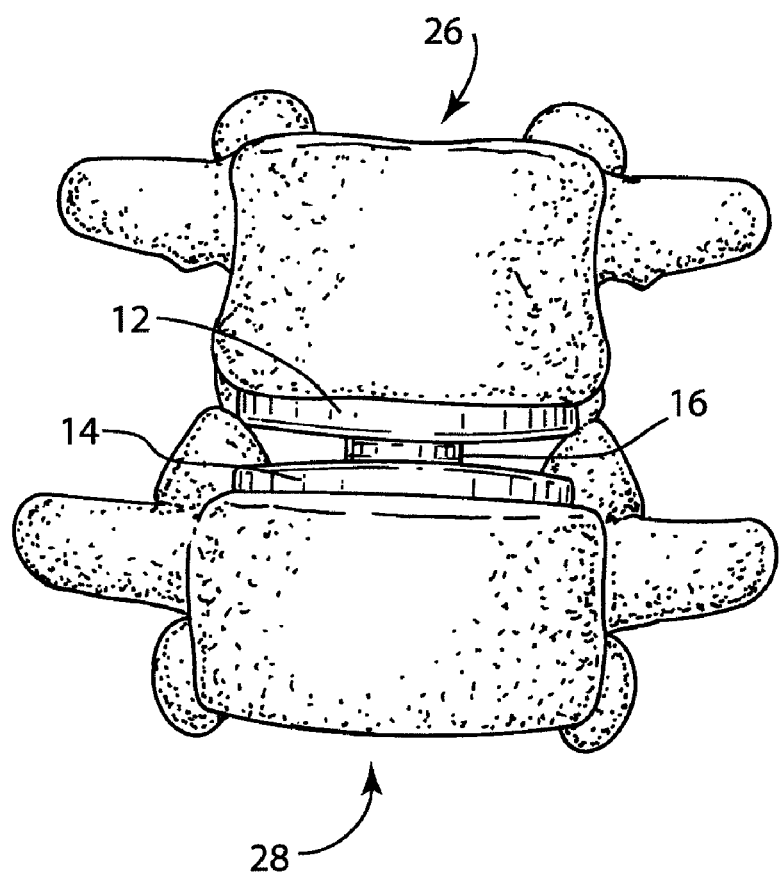
FIG. 6 is an anterior view of the implant depicted in FIG. 5.

Both upper and lower parts 12 and 14 each have an outer surface 24. As known in the art, outer surfaces 24 are each designed to contact an adjacent vertebrae, such as upper and lower vertebrae 26 and 28 depicted in FIGS. 2-6. As shown in FIGS. 2-4, vertebra 28 (and similar vertebrae in general) includes a relatively rigid cortical rim 30 of bone which surrounds less rigid cancellous bone 32. Prior art vertebral implants were designed to cover cortical rim 30. However, such coverage results in multiple points (or areas) of contact which are not needed. Thus, implant 10 of the present invention provides a more compact and hence easier to insert implant which still has a good and sufficient contact with the adjacent vertebrae.

It is thus a feature of the present invention that outer surfaces 24 are designed or sized to provide three distinct points (or small areas) of contact 34a, 34b and 34c (or collectively, points 34) with the adjacent cortical rim 30 as shown in FIG. 4. It will be appreciated that points of contact 34 shown in FIG. 4 are those of outer surface 24 of upper part 12 which would contact upper vertebra 26 (not shown) but in the same manner as the underlying points of contact 34 of lower part 14 (which are not seen because they are covered by upper part 12) contact lower vertebra 28 which is shown. It will be noted that outer surface 24 also includes a series of small teeth or spikes 36 or other such protrusions upstanding therefrom which serve to anchor upper and lower parts 12 and 14 in place after implantation as well known in the art.

As noted above, outer surface 24 is shaped with a major convex side according to the present invention to present a footprint so that only three points of contact 34 are provided thereby. As the size of vertebrae vary depending on location and on the individual user, implant 10 will be tailored to the individual so that only three points of contact 34 are made. This sizing of the footprint of outer surface 24 is conveniently determined by choosing the footprint of outer surface 24 to be located within the footprint of cortical rim 30 as shown. The points of contact 34 are left and right lateral-anterior points 34a and 34c which are preferably symmetrically located as shown, and a posterior point 34b. Conveniently, the footprint of the outer surface 24 includes opposed ends which provide the left and right lateral-anterior points 34a and 34c. Suitable footprints to provide the three points 34 of contact include: a) a convexo-concave footprint as shown by implant 10 in FIGS. 1-4 (and by implant 210 in FIG. 8); b) a D-shaped footprint as shown by implant 110 in FIG. 7; or c) a kidney shaped footprint as shown by implant 310 in FIGS. 9 and 11.

The use of such a small footprint and only three points of contact 34 with one being posterior or anterior also makes it possible for implants 10, 110, 210 and 310 to have a relatively narrow or small maximum width between left and right points 34a and 34c as evident from the three footprints discussed above. This narrow maximum width, particularly where augmented by a longitudinal concavity or inward bowing as with implants 10, 210 and 310, permits implants 10, 110, 210 and 310 to be inserted between adjacent vertebrae 26 and 28 through a smaller incision than if the implant spanned cortical rim 30 in all directions. In FIGS. 2-4, it will also be appreciated that the size and shape of implant 10 also makes the implanting of implant 10 from the angle shown and along the path depicted easy to accomplish.

Figure 7:
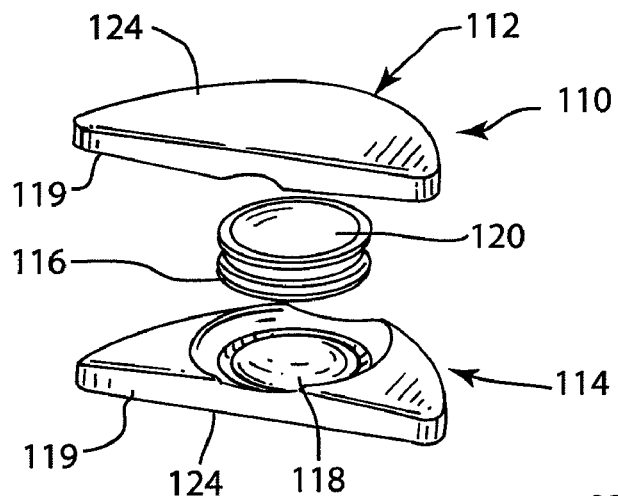
FIG. 7 is a perspective exploded view of an alternatively shaped implant of the present invention.

Implant 110 depicted in FIG. 7 discloses upper and lower parts 112 and 114 having outer surfaces 124 which present a D shaped footprint. As with FIG. 1, as noted above, insert 116 shows the upper concavity thereof (opposite the similar lower concavity thereof).

Figure 8:
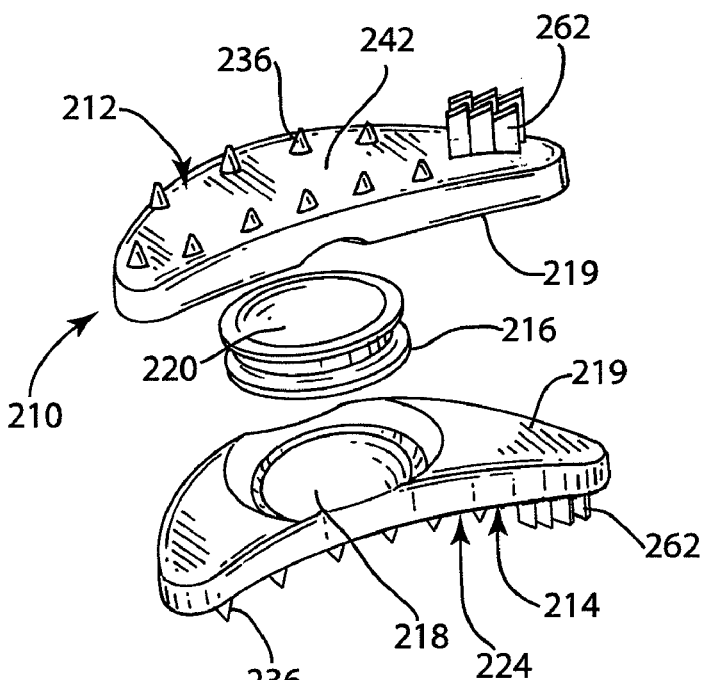
FIG. 8 is a perspective exploded view of an implant similar to FIG. 1 but showing a modification of the invention.

Depicted in FIG. 8 is an implant 210 which is also convexo-concave shaped like implant 10. However, implant 210 includes a keel 262 extending from each of outer surfaces 224 adjacent an opposed or longitudinal end thereof, and preferably the opposed end which is inserted last between vertebrae 26 and 28 (see FIG. 3) with the opposite longitudinal end then preferably having a slight chamfer to ease insertion. Each keel 262 serves to anchor the associated upper and lower parts 212 and 214 of implant 210 in place in a provided cutout or slot in adjacent vertebrae 26 and 28 after implantation as known in the art, in addition to the anchoring provided by the small spikes 236 also shown in FIG. 8. Keel 262 is depicted as curved or arced to match arced insertion path along which implant 210 would be implanted between the vertebrae (as shown by the three positions of implant 10 shown in FIGS. 2-4); though if implant 262 is implanted along a straight direction, keel 262 would instead be straight. If desired, two or more keels positioned along an arc or straight line could also be provided. The cutout required for keel 262 could be made in advance of implantation, or keel 262 could be self-cutting having chisel-like cutting edges at the introduction end as known in the art.

Figure 9:
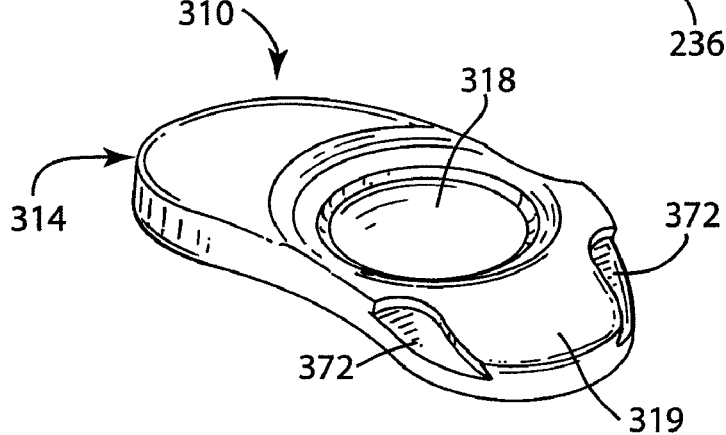
FIG. 9 is a perspective view of a component of an alternatively shaped implant of the present invention showing a modification of the invention.

In FIG. 9, an entire implant is identified by the numeral 310, although only lower part 314 thereof is shown in detail. The upper part 312 is a mirror image thereof, and the insert the same as the above described insert 16. Lower part 314 has an outer surface 324 which presents a kidney shaped footprint as shown. Also shown on lower part 314 are an opposed pair of cutouts 372 in inner surface 319. Cutouts 372 are dovetail shaped, that is, the vertical walls thereof are angled inwardly (or each toward the other cutout 372), and cutouts 372 are also preferably are longitudinally angled centrally inwardly or converging toward one another (or toward convexity 318) as they extend from the adjacent opposed end. Cutouts 372 are provided so that an instrument with a pair of matingly shaped engaging members can securely grasp lower part 314 (and similarly upper part 312) in order to insert implant 310 between vertebrae 26 and 28 as generally known in the art; and the added security of having both the dovetails shape and convergence allows cutouts 372 to be usable as well to reposition or even remove implant 310 as required. Of course, cutouts 372 could also be parallel to one another rather than converging if desired if less holding power is needed with the instrument.

Figure 10:
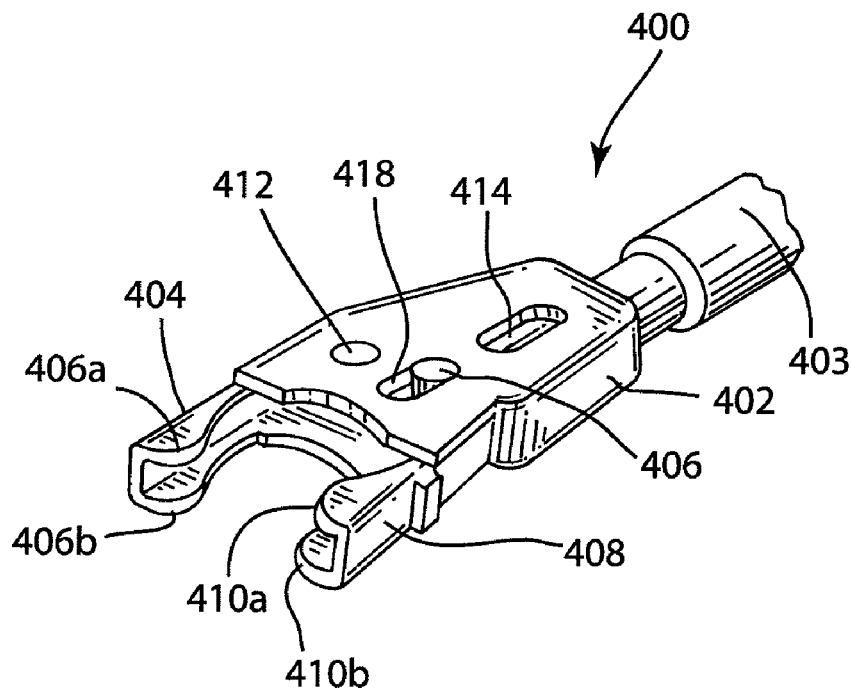
FIG. 10 shows the operative portion of an instrument used for insertion of an implant according to the present invention.
Figure 11:
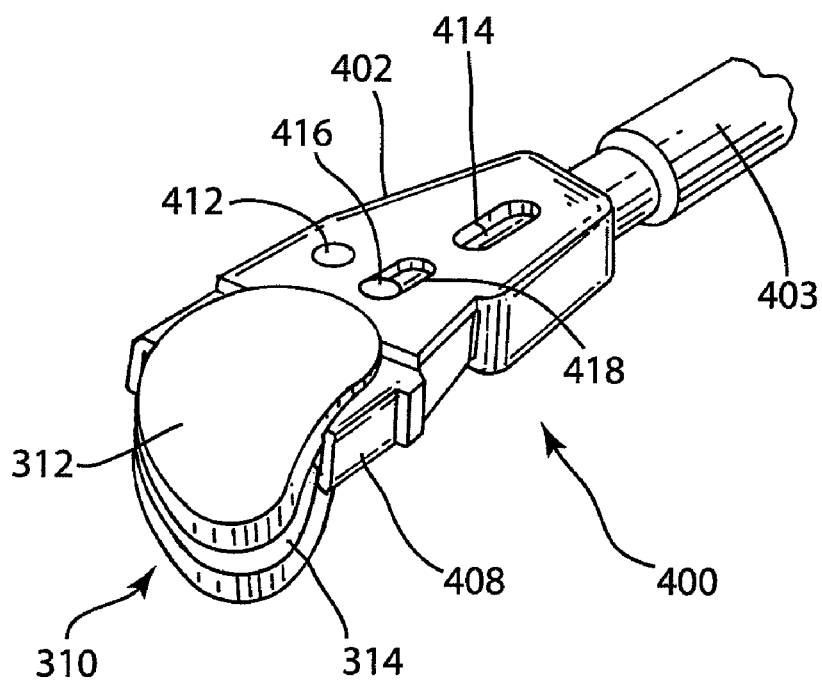
FIG. 11 shows an implant having components as in FIG. 9 being engaged by the instrument depicted in FIG. 10.

Depicted in FIGS. 10 and 11 is a portion of an insertion instrument 400 which can be used for insertion of implant 310 (or the other disclosed implants if they are provided with cutouts 372). Instrument 400 includes a base 402 attached to an inserter shaft 403. Extending distally from base 402 (away from inserter shaft 403) is a longitudinal fixed arm 404. Fixed arm 404 is shaped with top and bottom laterally-inwardly directed projections 406a and 406b. Projections 406 are designed to fit matingly in cutouts 372, and thus have a mating dovetail design. Laterally opposite to fixed arm 404 is a movable arm 408 having top and bottom laterally-inwardly directed projections 410a and 410b which are similarly shaped as projections 406 but oppositely directed. Like projections 406, projections 410 are designed to fit matingly in cutouts 372 but on the opposite side of implant 310. As known in the art, movable arm 408 is movable about a pivot 412 provided in base 402 toward fixed arm 404, and this movement is accomplished by a rod 414 guided in inserter shaft 403 which is forced against a pin 416 integral with movable arm 408 and trapped in slot 418 of base 402.

In use, instrument 400 is used to grasp implant 310 by placing projections 406 and 410 on either sides of implant 310 and adjacent respective cutouts 372. Then, by manipulation of rod 414, movable arm 408 is moved towards fixed arm 404 so that projections 406 and 410 are received in and then locked in cutouts 372. Once projections 406 and 410 are locked in place in cutouts 372, implant 310 is securely attached to base 402 so that implant 310 can be inserted between vertebrae by manipulation of inserter shaft 403 as known in the art.

While the present invention has been described with respect to exemplary embodiments thereof, it will be understood by those of ordinary skill in the art that variations and modifications can be effected within the scope and spirit of the invention.

We claim:

1. A method of implanting an intervertebral implant between adjacent vertebrae, the intervertebral implant having an upper part and a lower part, each of the upper part and lower part having an inner surface, an outer surface and a convexo-concave or kidney-shape, the adjacent vertebrae having cortical rims with left and right lateral walls, a posterior wall and an anterior wall, the convexo-concave or kidney-shape of each of the upper and lower parts defining first and second opposed lateral ends and a posterior nose, the method comprising the steps of:
    a) creating a small incision to gain access to an intervertebral space between the adjacent vertebrae proximate the anterior walls and one of the left and right lateral walls;
    b) engaging the intervertebral implant with an instrument;
    c) inserting the intervertebral implant into the intervertebral space along an arc-shaped anterolateral path; and
    d) positioning the implant in the intervertebral space such that the first lateral ends engage left lateral-anterior points of the left walls, the second lateral ends engage right lateral-anterior points of the right walls and the posterior noses engage posterior points of the posterior walls thereby defining three points of contact between each of the upper and lower parts and the cortical rim of each of the adjacent vertebrae, a footprint of the outer surface of each part of the intervertebral implant positioned within the adjacent cortical rim, the three points of contact defining the only engagement between each of the upper and lower parts and the cortical rim of the adjacent vertebrae, respectively.

2. The method of implanting the intervertebral implant of claim 1, comprising the further step of:
    e) preparing an arc-shaped cutout in both of the adjacent vertebrae prior to step (c) to match a portion of the arc-shaped anterolateral path.

3. The method of implanting the intervertebral implant of claim 2, wherein the each of the upper and lower parts includes one of a curved and arced keel on the outer surface, the one of the curved and arced keel positioned in the arc-shaped cutout following step (d).

4. The method of implanting the intervertebral implant of claim 1 comprising the further step of:
    e) anchoring the intervertebral implant to at least one of the adjacent vertebrae, wherein the outer surface of at least one of the upper and lower parts includes at least one vertebra engaging protrusion that engages the at least one of the adjacent vertebrae.

5. The method of implanting the intervertebral implant of claim 1, wherein the at least one of the upper and lower parts includes at least one of a curved and arced keel on the outer surface, the at least one of the curved and arced keel self-cutting a cutout in at least one of the adjacent vertebrae in steps (c) and (d).

6. The method of implanting the intervertebral implant of claim 5, wherein the at least one of the curved and arced keel includes a chisel-like cutting edge to accommodate the self-cutting of the cutout.

7. The method of implanting the intervertebral implant of claim 1, wherein the upper and lower parts include a pair of instrument receiving cutouts on the inner surface extending to an adjacent outer edge thereof, the instrument grasping the intervertebral implant at the pair of instrument receiving cutouts in step (b).

8. The method of implanting the intervertebral implant of claim 7, wherein the pair of instrument receiving cutouts is angled centrally inwardly to promote secure grasping of the intervertebral implant by the instrument in step (b).

9. The method of implanting the intervertebral implant of claim 8, wherein the pair of instrument receiving cutouts is dovetail-shaped in cross section to further promote secure grasping of the intervertebral implant by the instrument in step (b).

10. A method of implanting an intervertebral implant between adjacent vertebrae, the intervertebral implant having an upper part and a lower part, each of the upper part and lower part having an inner surface, an outer surface and a convexo-concave or kidney-shape, the adjacent vertebrae having cortical rims with left and right lateral walls, a posterior wall and an anterior wall, the convexo-concave or kidney-shape of each of the upper and lower parts defining first and second opposed lateral ends and a posterior nose, the method comprising the steps of
    a) creating an incision to gain access to an intervertebral space between the adjacent vertebrae proximate the anterior walls and one of the left and right lateral walls;
    b) engaging the intervertebral implant with an instrument;
    c) inserting the intervertebral implant into the intervertebral space along an arc-shaped anterolateral path, the arc-shaped anterolateral path extending into the intervertebral space through a window defined by the one of the left and right lateral walls such that a footprint of the outer surface of each part of the intervertebral implant extends through the window and substantially avoids extending through gaps defined by the posterior and anterior walls, respectively; and
    d) positioning the implant in the intervertebral space such that the first lateral ends of the upper and lower parts engage left lateral-anterior points of the left walls, the second lateral ends of the upper and lower parts engage right lateral-anterior points of the right walls and the posterior noses of the upper and lower parts engage posterior points of the posterior walls thereby defining six points of contact between the intervertebral implant and the cortical rims.

11. The method of implanting the intervertebral implant of claim 10, wherein the six points of contact define the only engagement between the intervertebral implant and the cortical rim of the adjacent vertebrae following step (d).

12. The method of implanting the intervertebral implant of claim 10, wherein the window defined by the one of the left and right lateral walls of step (c) is defined by the right lateral walls of the adjacent vertebrae, the intervertebral implant includes first and second keels extending generally perpendicularly from outer surfaces of the upper and lower parts, respectively, the first and second keels positioned proximate first lateral ends of the upper and lower parts, respectively, the first and second keels and the first lateral ends positioned proximate a right lateral-anterior points in step (d).

13. The method of implanting the intervertebral implant of claim 10, wherein the window defined by the one of the left and right lateral walls of step (c) is defined by the left lateral walls of the adjacent vertebrae, the intervertebral implant includes first and second keels extending generally perpendicularly from outer surfaces of the upper and lower parts, respectively, the first and second keels positioned proximate second lateral ends of the upper and lower parts, respectively, the first and second keels and the first lateral ends positioned proximate a left lateral-anterior points in step (d).

14. A method of implanting an intervertebral implant between adjacent inferior and superior vertebrae, the intervertebral implant having an upper part and a lower part, with each of the upper and lower parts having an outer surface with a convexo-concave or kidney shape, each adjacent vertebra having a cortical rim with left and right lateral walls, a posterior wall and an anterior wall, the convexo-concave or kidney shape of each outer surface defining first and second opposed lateral ends and a posterior nose, the method comprising the steps of:

a) creating a small incision to gain access to an intervertebral space between the adjacent vertebrae proximate the anterior wall and one of the left and right lateral walls;
b) engaging the intervertebral implant with an instrument;
c) inserting the intervertebral implant into the intervertebral space through the incision with the instrument along an arc-shaped anterolateral path; and
d) positioning the intervertebral implant in the intervertebral space relative to an adjacent vertebrae such that the first lateral end of the lower part engages a left lateral-anterior point of the left wall of the inferior vertebra, the second lateral end of the lower part engages a right lateral-anterior point of the right wall of the inferior vertebra and the posterior nose of the lower part engages a posterior point of the posterior wall of the inferior vertebra, thereby defining three points of contact between the lower part and the cortical rim of the inferior vertebra, a footprint of each of the upper and lower parts is positioned within the cortical rim of the inferior and superior vertebrae, the three points of contact define the only engagement between the lower part and the cortical rim of the inferior vertebra.

* * * * *